(12) United States Patent
Lee et al.

(10) Patent No.: US 12,603,178 B2
(45) Date of Patent: Apr. 14, 2026

(54) APPARATUS AND METHODS FOR SUPPORTING MEDICAL DECISIONS

(71) Applicant: University-Industry Cooperation Group of Kyung Hee University, Gyeonggi-do (KR)

(72) Inventors: Sung Young Lee, Gyeonggi-do (KR); Hao Hua-Cam, Gyeonggi-do (KR); Ubaid Ur Rehman, Gyeonggi-do (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 364 days.

(21) Appl. No.: 18/123,449

(22) Filed: Mar. 20, 2023

(65) Prior Publication Data

US 2024/0153630 A1      May 9, 2024

(30) Foreign Application Priority Data

Nov. 4, 2022      (KR) ........................ 10-2022-0146478

(51) Int. Cl.
| | |
|---|---|
| *G16H 15/00* | (2018.01) |
| *G06V 10/82* | (2022.01) |
| *G06V 30/18* | (2022.01) |
| *G16H 30/40* | (2018.01) |
| *G16H 50/20* | (2018.01) |

(52) U.S. Cl.
CPC ............. *G16H 50/20* (2018.01); *G06V 10/82* (2022.01); *G06V 30/18* (2022.01); *G16H 15/00* (2018.01); *G16H 30/40* (2018.01)

(58) Field of Classification Search
CPC ........ G16H 50/20; G16H 15/00; G16H 30/40; G16H 50/70; G16H 10/20; G16H 30/20; G16H 50/50; G16H 70/60; G06V 10/82; G06V 30/18; G06V 2201/03; G06F 40/205; G06F 40/30; G06N 3/0455; G06N 3/0464
See application file for complete search history.

(56) References Cited

U.S. PATENT DOCUMENTS

2019/0206517 A1* 7/2019 Devarakonda ......... G16H 50/70

FOREIGN PATENT DOCUMENTS

| | | | | | |
|---|---|---|---|---|---|
| CN | 111095426 A | * | 5/2020 | .............. | G06N 3/04 |
| CN | 115206478 A | * | 10/2022 | | |
| KR | 10-2022-0105723 A | | 7/2022 | | |
| WO | WO-2010109351 A1 | * | 9/2010 | .......... | G06F 19/321 |
| WO | WO-2021015937 A1 | * | 1/2021 | ......... | G06F 16/3347 |

* cited by examiner

*Primary Examiner* — Huo Long Chen
(74) *Attorney, Agent, or Firm* — The PL Law Group, PLLC

(57)      ABSTRACT

A medical decision supporting apparatus according to an embodiment may include a visual and linguistic neural learner, which receives a medical image and extracts visual embedding, a cause miner, which extracts a predetermined index based on the visual embedding and pretrained embedding, and outputs a predetermined cause for the medical image based on a hash map including at least one index-concept pair and the extracted predetermined index, a logical reasoner, which generates a medical report based on the visual embedding, a background knowledge graph, and the predetermined cause, and a proof inference unit, which generates an answer including a proof for a user's question about the medical image based on the predetermined cause and the medical report.

14 Claims, 8 Drawing Sheets

Figure 5:
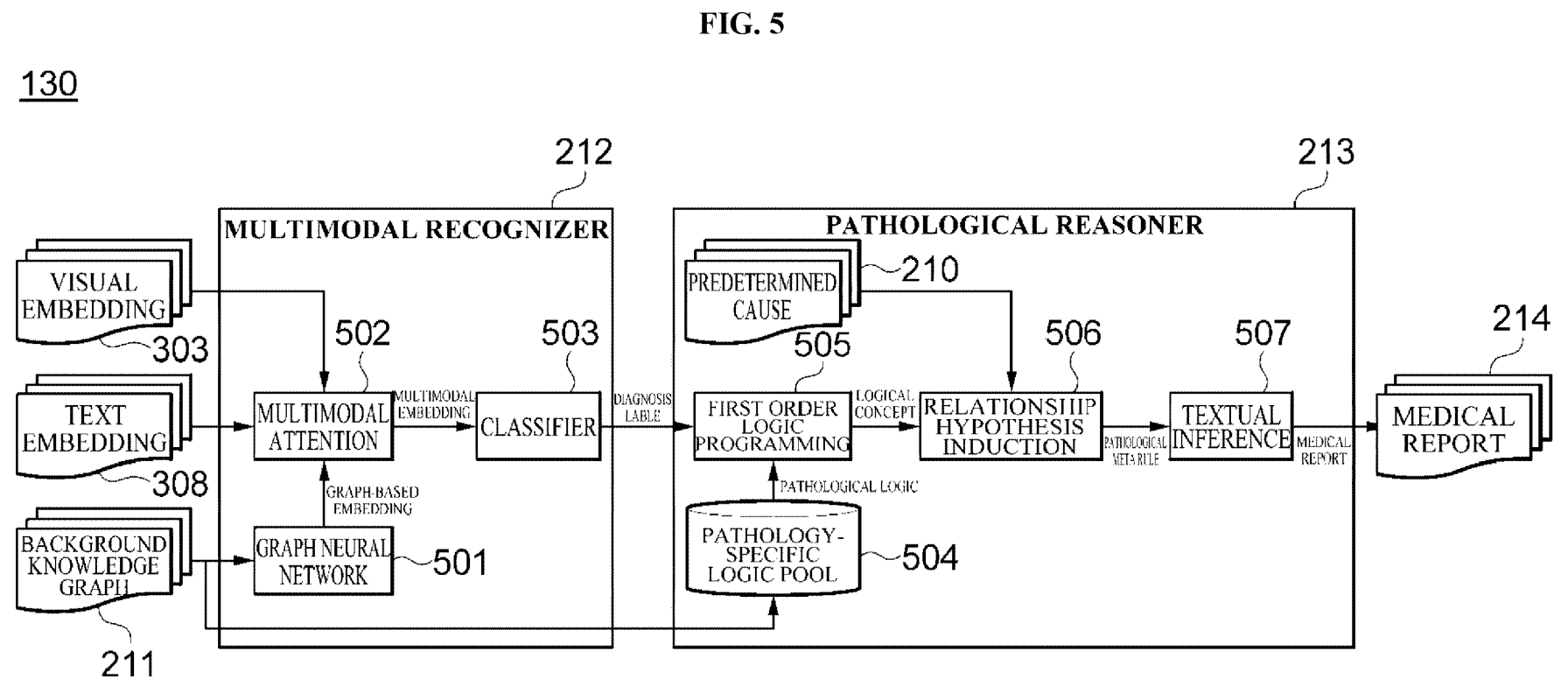

MULTIMODAL RECOGNIZER 212

VISUAL EMBEDDING 303

TEXT EMBEDDING 308

BACKGROUND KNOWLEDGE GRAPH 211

GRAPH NEURAL NETWORK 501

MULTIMODAL ATTENTION 502

GRAPH-BASED EMBEDDING

MULTIMODAL EMBEDDING

CLASSIFIER 503

DIAGNOSIS LABLE

PATHOLOGICAL REASONER 213

PREDETERMINED CAUSE 505

PATHOLOGY-SPECIFIC LOGIC POOL 504

FIRST ORDER LOGIC PROGRAMMING 505

PATHOLOGICAL LOGIC

LOGICAL CONCEPT

RELATIONSHIP HYPOTHESIS INDUCTION 506

PATHOLOGICAL META-RULE

210

TEXTUAL INFERENCE 507

MEDICAL REPORT

MEDICAL REPORT 214

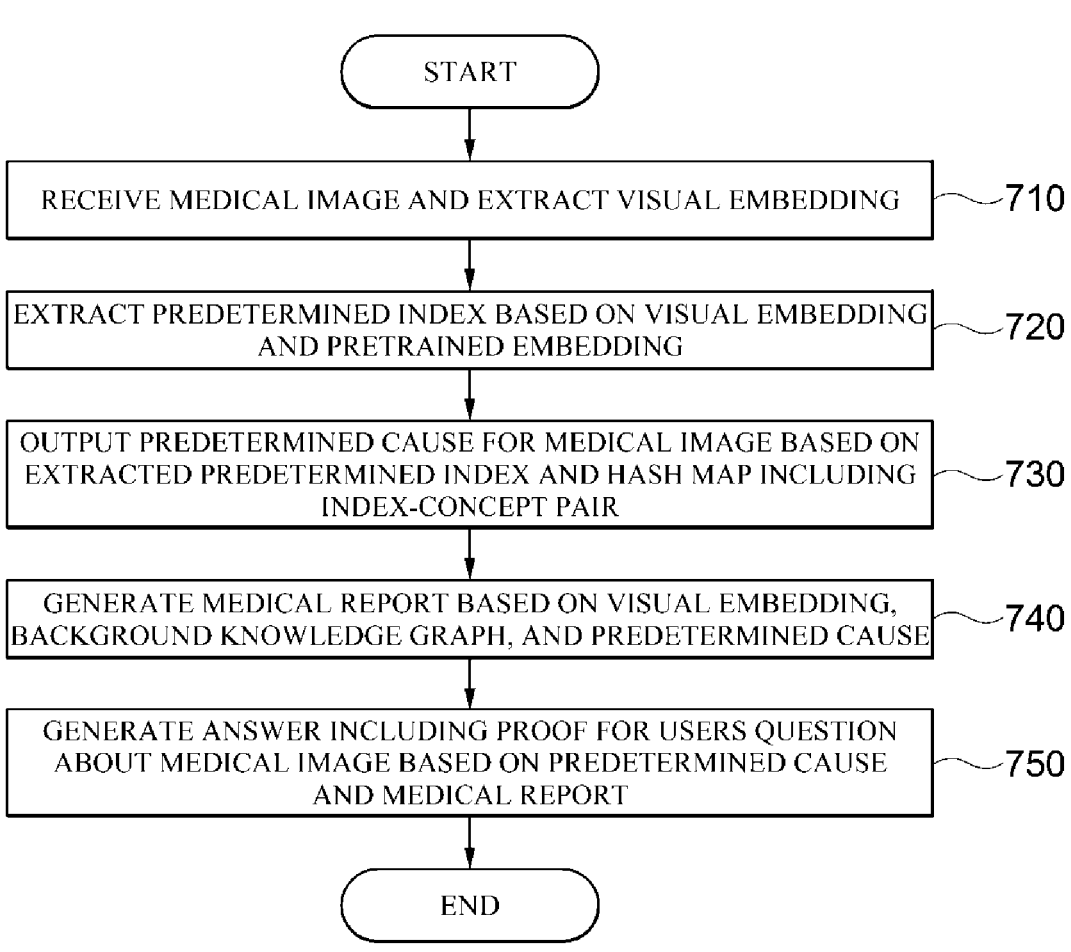

START

RECEIVE MEDICAL IMAGE AND EXTRACT VISUAL EMBEDDING ⌐~710

EXTRACT PREDETERMINED INDEX BASED ON VISUAL EMBEDDING AND PRETRAINED EMBEDDING ⌐~720

OUTPUT PREDETERMINED CAUSE FOR MEDICAL IMAGE BASED ON EXTRACTED PREDETERMINED INDEX AND HASH MAP INCLUDING INDEX-CONCEPT PAIR ⌐~730

GENERATE MEDICAL REPORT BASED ON VISUAL EMBEDDING, BACKGROUND KNOWLEDGE GRAPH, AND PREDETERMINED CAUSE ⌐~740

GENERATE ANSWER INCLUDING PROOF FOR USERS QUESTION ABOUT MEDICAL IMAGE BASED ON PREDETERMINED CAUSE AND MEDICAL REPORT ⌐~750

END

APPARATUS AND METHODS FOR SUPPORTING MEDICAL DECISIONS

CROSS-REFERENCE TO RELATED APPLICATION AND CLAIM OF PRIORITY

This application claims the benefit under 35 USC § 119 of Korean Patent Application No. 10-2022-0146478, filed on Nov. 4, 2022, in the Korean Intellectual Property Office, the entire disclosure of which is incorporated herein by reference for all purposes.

BACKGROUND

1. Field

The present disclosure relates to a medical decision supporting apparatus and method for generating an answer including a proof in response to a user's query on a medical image.

2. Description of Related Art

Recently, researches have been actively carried out to develop a technology of analyzing a medical image using an artificial neural network. Korean Patent Application Publication No. 10-2022-0105723 (Jul. 28, 2022) discloses a method for identifying a change between medical images captured at different points in time with respect to the same diagnosis subject by using a pretrained medical image analysis model.

However, according to the prior art, only a result is provided without grounds for image analysis, and thus it may be difficult for a doctor to trust an analysis result at a clinical stage.

SUMMARY

The present disclosure provides a medical decision supporting apparatus and method for generating an answer including a proof in response to a user's query on a medical image.

According to one aspect, a medical decision supporting apparatus may include a visual and linguistic neural learner, which receives a medical image and extracts visual embedding, a cause miner, which extracts a predetermined index based on the visual embedding and pretrained embedding, and outputs a predetermined cause for the medical image based on a hash map including at least one index-concept pair and the extracted predetermined index, a logical reasoner, which generates a medical report based on the visual embedding, a background knowledge graph, and the predetermined cause, and a proof inference unit, which generates an answer including a proof for a user's question about the medical image based on the predetermined cause and the medical report.

The visual and linguistic neural learner may include a visual encoder, which extracts the visual embedding from the medical image; a text encoder, which extracts text embedding from text data about the medical image, and a cross-modal decoder, which extracts multimodal embedding based on the visual embedding and the text embedding.

The visual encoder may include at least one convolutional layer including a convolutional kernel, batch normalization layer, and nonlinear activation layer, and a global pooling layer.

The text encoder may include a word embedding layer, a positional embedding layer,
an addition layer, and at least one encoder, wherein each of the at least one encoder may output the text embedding based on the input text data.

The cross-modal decoder may include at least one decoder, wherein each of the at least one decoder may output the multimodal embedding based on at least one of the visual embedding that is an output from the visual encoder, the text embedding that is an output from the text encoder, or multimodal embedding that is an output form a previous-stage decoder.

The cause miner may include: a modality-agnostic causality decoder, which receives an input of the visual embedding and outputs a causal concept; a causal triple embedding & concept repository, which stores the visual embedding and the causal concept; a nearest causal candidate retriever, which extracts an index of pretrained embedding that is most similar to input visual embedding among pretrained embedding stored in the causal triple embedding & concept repository by using at least one of cosine similarity or Euclidean similarity; and a causal concept inference unit, which matches a concept in the extracted index based on the extracted index and the hash map stored in the causal triple embedding & concept repository, and transforms the matched concept into a sentence to output an associated causal expression.

The logical reasoner may include: a multimodal recognizer, which generates multimodal embedding based on the visual embedding, text embedding, and graph-based embedding, and generates a diagnosis label based on the multimodal embedding; and a pathological reasoner, which generate a logical concept based on the diagnosis label and pathological logic, and generates the medical report by transforming a pathological meta rule generated based on the logical concept and the predetermined cause into a natural language.

The proof inference unit may include: a visual question answer interpreter, which receives an input of the user's question about the medical image, extracts a type of a visual question and answer, and determines a visual question answer (VQA) triple according to a VQA type; a semantic parser, which receives an input of the VQA triple, the predetermined cause, and the medical report, extracts a sentence related to the visual question answer from the predetermined cause and the medical report, and constructs a hierarchy in a form of entity, sentence, and context for the extracted sentence; and a factual reasoning & verifier, which receives an input of the VQA triple and a duplication-filtered hierarchy in a form of entity, sentence, and context, and generates a proof for the user's question.

According to one aspect, a medical decision supporting method may include: a visual and linguistic neural learning step of receiving a medical image and extracting visual embedding; a cause mining step of extracting a predetermined index based on the visual embedding and pretrained embedding, and outputting a predetermined cause for the medical image based on a hash map including at least one index-concept pair and the extracted predetermined index; a logical reasoning step of generating a medical report based on the visual embedding, a background knowledge graph, and the predetermined cause; and a proof inference step of generating an answer including a proof for a user's question about the medical image based on the predetermined cause and the medical report.

The visual and linguistic neural learning step may include extracting the visual embedding from the medical image, extracting text embedding from text data about the medical image, and extracting multimodal embedding based on the visual embedding and the text embedding.

In the visual and linguistic neural learning step, a visual encoder may be used, which includes at least one convolutional layer including a convolutional kernel, batch normalization layer, and nonlinear activation layer, and a global pooling layer.

In the visual and linguistic neural learning step, a text encoder may be used, which includes a word embedding layer, a positional embedding layer, an addition layer, and at least one encoder, wherein each of the at least one encoder may output the text embedding based on the input text data.

In the visual and linguistic neural learning step, a cross-modal decoder may be used, which includes at least one decoder, wherein each of the at least one decoder may output the multimodal embedding based on at least one of the visual embedding that is an output from a visual encoder, the text embedding that is an output from a text encoder, or multimodal embedding that is an output form a previous-stage decoder.

The cause mining step may include receiving an input of the visual embedding and outputting a causal concept, storing the visual embedding and the causal concept, extracting an index of pretrained embedding that is most similar to input visual embedding among pretrained embedding stored in a causal triple embedding & concept repository by using at least one of cosine similarity or Euclidean similarity, matching a concept in the extracted index based on the extracted index and a hash map stored in the causal triple embedding & concept repository, and transforming the matched concept into a sentence to output an associated causal expression.

The logical reasoning step may include generating multimodal embedding based on the visual embedding, text embedding, and graph-based embedding, generating a diagnosis label based on the multimodal embedding, generating a logical concept based on the diagnosis label and pathological logic, and generating the medical report by transforming a pathological meta rule generated based on the logical concept and the predetermined cause into a natural language.

The proof inference step may include receiving an input of the user's question about the medical image, extracting a type of a visual question and answer, determining a visual question answer (VQA) triple according to a VQA type, receiving an input of the VQA triple, the predetermined cause, and the medical report, extracting a sentence related to the visual question answer from the predetermined cause and the medical report, constructing a hierarchy in a form of entity, sentence, and context for the extracted sentence, receiving an input of the VQA triple and a duplication-filtered hierarchy in a form of entity, sentence, and context, and generating a proof for the user's question.

According to one aspect, a non-transitory computer readable storage medium may store at least one program including one or more instructions that, when executed by an electronic device having at least one processor and a memory, cause the electronic device to execute the method.

BRIEF DESCRIPTION OF THE DRAWINGS

FIG. 2 is a configuration diagram illustrating a detailed configuration of a medical decision supporting apparatus according to an embodiment.

FIG. 4 is a configuration diagram illustrating a cause miner according to an embodiment.

FIG. 5 is a configuration diagram illustrating a logical reasoner according to an embodiment.

FIG. 7 is a flowchart illustrating a medical decision supporting method according to an embodiment.

Figure 1:
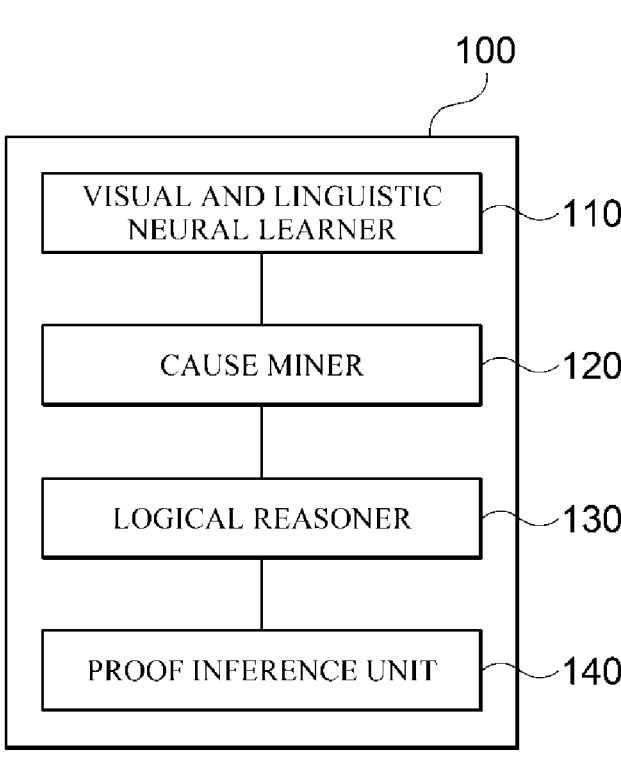
FIG. 1 is a configuration diagram illustrating a medical decision supporting apparatus according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, embodiments of the present disclosure will be described in detail with reference to the accompanying drawings. Detailed descriptions of well-known functions or configurations will be omitted in order not to unnecessarily obscure the focus of the present disclosure. The terms used below are defined in consideration of functions in the present disclosure, but may vary in accordance with customary practice or the intention of a user or an operator. Therefore, the terms should be defined based on whole content throughout the present specification.

Hereinafter, a medical decision supporting apparatus and method will be described in detail with reference to the drawings.

FIG. 1 is a configuration diagram illustrating a medical decision supporting apparatus according to an embodiment.

Referring to FIG. 1, a medical decision supporting apparatus 100 may include a visual and linguistic neural learner 110, which receives a medical image and extracts visual embedding, a cause miner 120, which extracts a predetermined index based on the visual embedding and pretrained embedding, and outputs a predetermined cause for the medical image based on a hash map including at least one index-concept pair and the extracted predetermined index, a logical reasoner 130, which generates a medical report based on the visual embedding, a background knowledge graph, and the predetermined cause, and a proof inference unit 140, which generates an answer including a proof for a user's question about the medical image based on the predetermined cause and the medical report.

According to an example, the visual and linguistic neural learner 110 may receive an input of a medical image and clinical text for the medical image in order to perform a neural learning process, and may extract embedding that is a feature vector indicating a basic attribute of medical data. The cause miner 120 may infer a predetermined cause of a visual manifestation from a medical image using a numerical result from the visual and linguistic neural learner 110.

According to an example, the logical reasoner 130 may generate a medical report through a logical reasoning model after comprehending a predetermined cause of a natural language or a concept interpretable by a human by using a background knowledge graph with respect to implicit findings in a visual and linguistic neural learning process. The proof inference unit 140 may provide an inferred answer to at least one question, raised by a doctor who is a user, about a medical image or diagnosis result together with a proof supporting the answer.

For example, a final output of a neural-symbolic coherent reasoning method provided by the medical decision supporting apparatus 100 may include a predetermined cause, a medical report, and an answer (when at least one question related to visual contents of an input medical image is provided) with a proof. Such a result may assist a doctor with making a medical decision.

Figure 2:
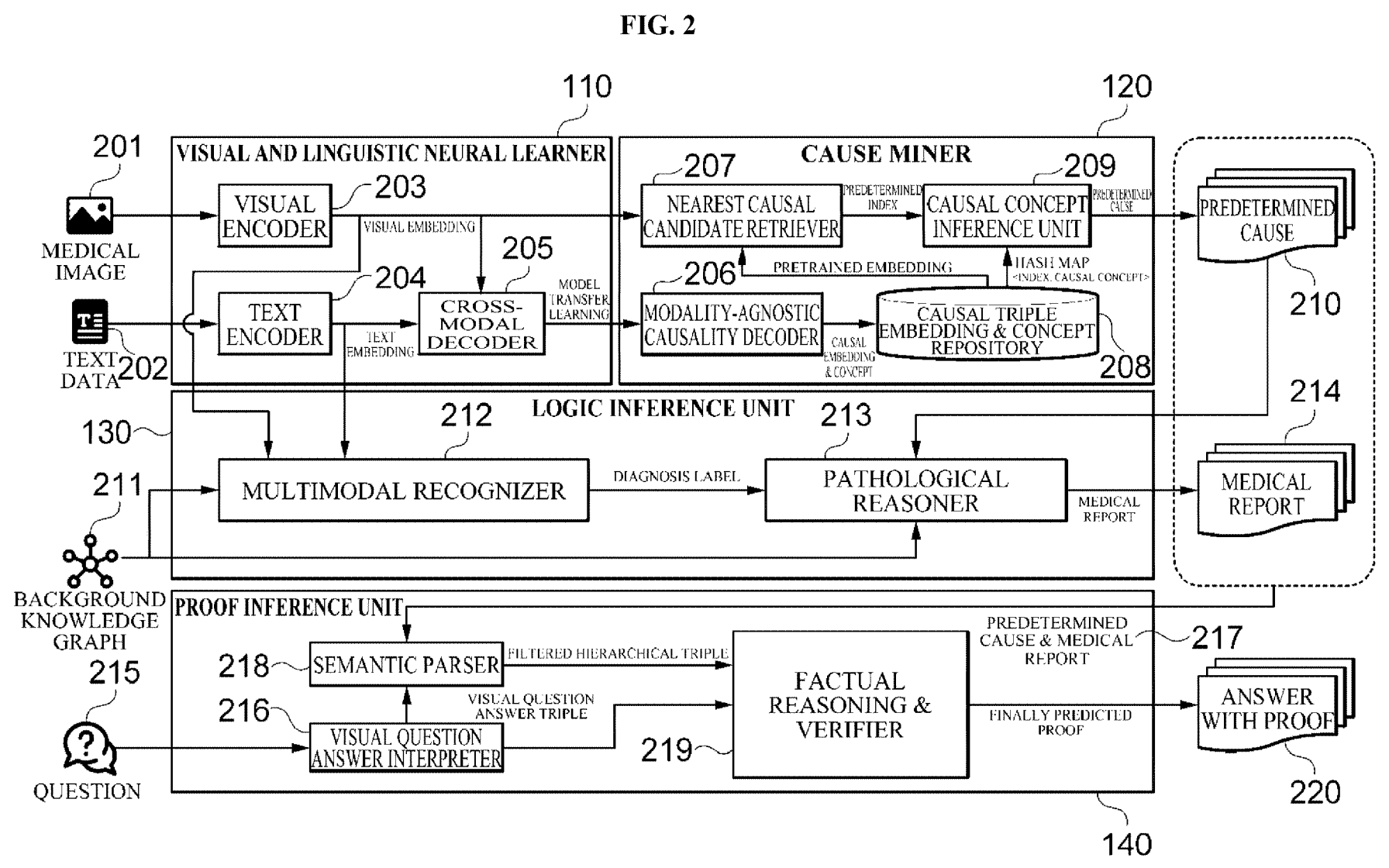

FIG. 2 is a configuration diagram illustrating a detailed configuration of a medical decision supporting apparatus according to an embodiment.

According to an embodiment, the visual and linguistic neural learner 110 may use a visual encoder 203 to extract visual embedding for delivering an inherent attribute of an input medical image 201 in a numerical vector form. A text encoder 204 may generate text embedding when given text data 202 for the input medical image.

For example, the visual embedding and the text embedding may be input to a cross-modal decoder 205, and an output from the cross-modal decoder 205 may be used in training with a visual linguistic task. The cross-modal decoder 205 pretrained with different visual linguistic tasks may be adopted as a modality-agnostic causality decoder 206 through a model transfer learning technique.

For example, when at least one of the visual embedding or the text embedding is given at a learning (offline) stage, the modality-agnostic causality decoder 206 may extract causal embedding and concept, and thereafter may store the same in a causal triple embedding & concept repository 208. A nearest causal candidate retriever 207 may generate a best predetermined index by receiving an input of visual embedding with reference to pretrained embedding in the causal triple embedding & concept repository 208 at a reasoning (online) stage.

According to an example, a causal concept inference unit 209 may generate a predetermined cause for a severity state of the input medical image by triggering a hash map including a pair of an index and concept in the causal triple embedding & concept repository 208.

According to an example, a multimodal recognizer 212 of the logical reasoner 130 may output a diagnosis label by receiving an input of the visual embedding and the text embedding together with a background knowledge graph 211. A pathological reasoner 213 may generate a medical report in natural language by receiving an input of the output diagnosis label, the predetermined cause inferred by the cause miner 120, and the background knowledge graph.

For example, a reasoning result of a proposed neural-symbolic coherent reasoning method may include a predetermined cause and a medical report. Furthermore, when a doctor inputs at least one clinical question about the input medical image, a reasoning procedure may be additionally used by the proof inference unit 140. For example, a visual question answer interpreter 216 may be enabled to generate a visual question-answer triple as an input to a sematic parser 218 and a factual reasoning & verifier 219, which are following components. The semantic parser 218 may use a previous reasoning result, i.e., the predetermined cause and the medical report, in order to infer a filtered hierarchical triple.

According to an example, the factual reasoning & verifier 219 may generate a finally predicted proof in order to support a theoretical basis of an answer to an input question based on symbol information given in a previous task.

Therefore, according to an embodiment, the medical decision supporting apparatus 100 may perform reasoning about a medical diagnosis problem through inference of a consistent multi-dimensional result including a text expression of a proof (supporting an inferred answer for VQA task), medical report, logic, and cause.

Figure 3:
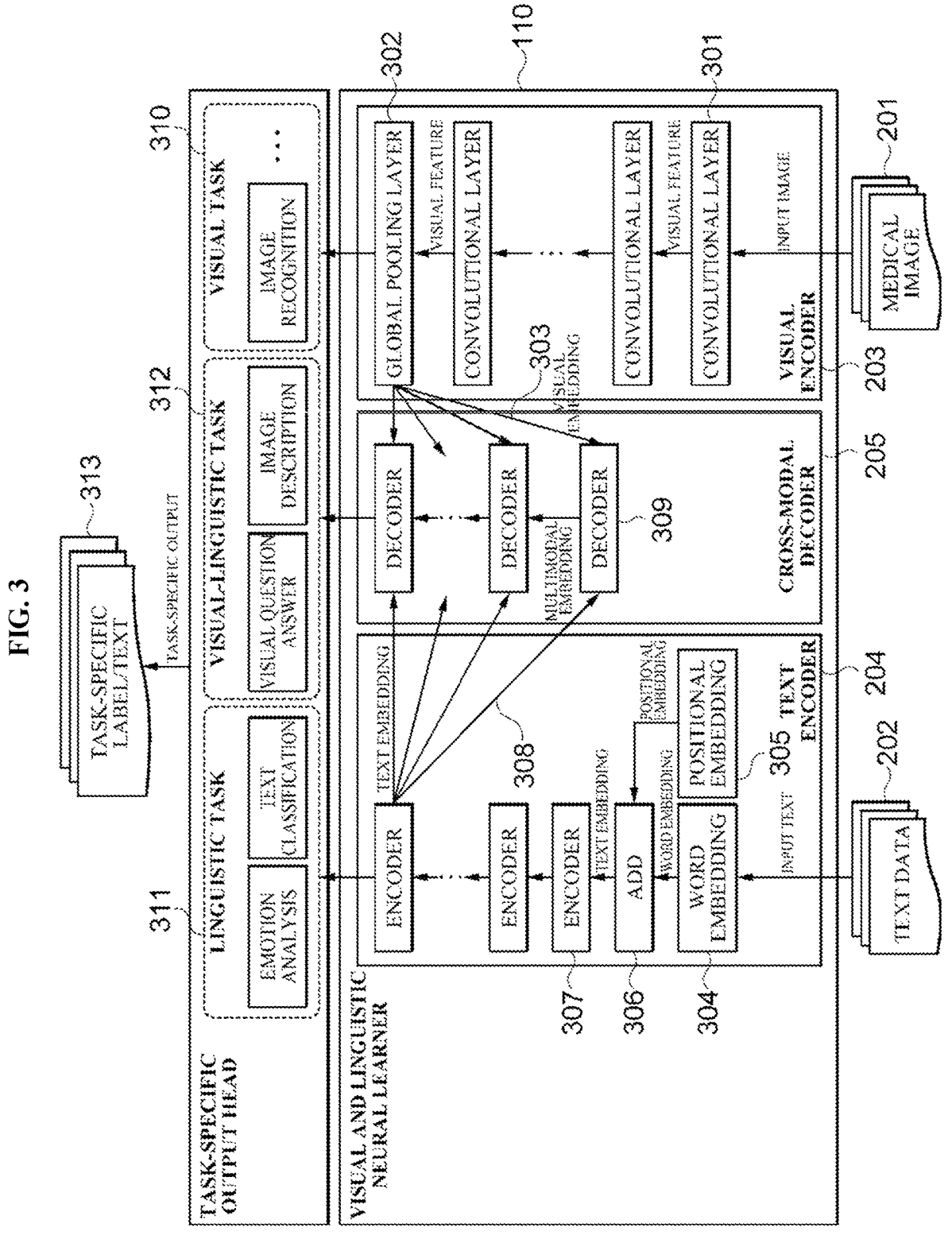
FIG. 3 is a configuration diagram illustrating a visual and linguistic neural learner according to an embodiment.

FIG. 3 is a configuration diagram illustrating a visual and linguistic neural learner according to an embodiment.

According to an embodiment, the visual and linguistic neural learner 110 may include the visual encoder 203, which extracts visual embedding from a medical image, the text encoder 204, which extracts text embedding from text data about the medical image, and the cross-modal decoder 205, which extracts multimodal embedding based on the visual embedding and the text embedding.

Referring to FIG. 3, the visual and linguistic neural learner 110 may be configured with the visual encoder 203, the text encoder 204, and the cross-modal decoder 205. Each component may be flexibly connected to various task-specific output heads so as to simultaneously or independently process a visual task (e.g., image recognition or classification, etc.), a linguistic task (e.g., emotion analysis, text classification, etc.), and a visual-linguistic task (e.g., answer to a visual question, image caption, etc.).

According to an example, an output from the visual and linguistic neural learner 110 may be a task-specific label or text, and an actual equivalent among the task-specific label and text may be widely used in a corresponding published data set. Therefore, the visual and linguistic neural learner 110 may learn a powerful function corresponding to each single input form independently in an end-to-end manner. As a result, the visual and linguistic neural learner 110 may effectively obtain a cross-modal expression without significantly depending on rich annotations of multimodal data.

According to an embodiment, the visual encoder 203 may include at least one convolutional layer including a convolutional kernel, batch normalization layer, and nonlinear activation layer, and a global pooling layer.

For example, the medical image 201 input to the visual encoder 203 may be manipulated by a sequential stack of at least one predefined convolutional layer, and each of the layers may be configured with a convolutional filter/kernel 301, a batch normalization layer, and a nonlinear activation layer (e.g., Sigmoid, Rectified Linear Unit, etc.). The global pooling layer 302 may transform a semantically visual feature into visual embedding indicating overall context information of whole image content. An output from the global pooling layer 302 may be used in learning a visual task in order to train with learnable parameters of convolutional layers, as described above.

According to an embodiment, the text encoder 204 may include a word embedding layer, a positional embedding layer, and an addition layer.

For example, the text encoder 204 may generate text embedding by processing input text based on a sequential stack of a word embedding layer 304, a positional embedding layer 305, an addition layer 306, and at least one predefined transformer-based encoder layer. Here, an intermediate result may be used in learning learnable parameters of the transformer-based encoder layer by learning the above-mentioned linguistic task.

According to an embodiment, the cross-modal decoder 205 may include at least one decoder, wherein each of the at least one decoder may output multimodal embedding based on at least one of visual embedding that is an output from the visual encoder, text embedding that is an output from the text encoder, or multimodal embedding that is an output form a previous-stage decoder.

For example, the cross-modal decoder 205 may include a sequential stack of a predefined number of at least one decoder layer, and may extract multimodal embedding by using visual embedding and text embedding respectively extracted by the visual encoder and the text encoder. A final output from the cross-modal decoder 205 may be used in learning a visual linguistic task in order to train with learnable parameters of the decoder layer.

For example, the modality-agnostic causality decoder 206 may be configured by adopting the cross-modal decoder 205 pretrained in the cause miner 120 through a model transfer learning technique.

Figure 4:
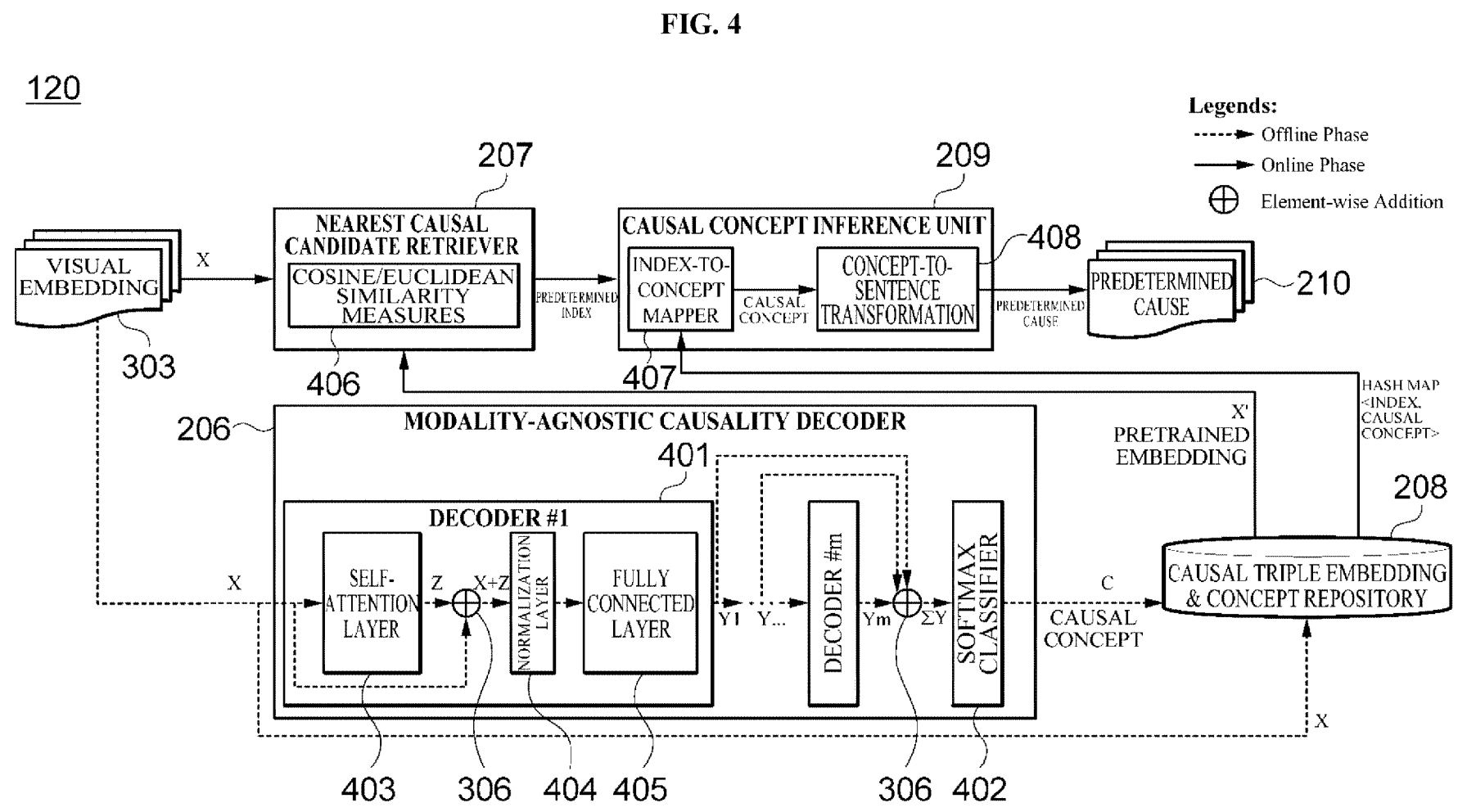

FIG. 4 is a configuration diagram illustrating a cause miner according to an embodiment.

According to an embodiment, the causer miner 120 may include the modality-agnostic causality decoder 206, which receives an input of visual embedding and outputs a causal concept, the causal triple embedding & concept repository 208, which stores the visual embedding and causal concept, the nearest causal candidate retriever 207, which extracts an index of pretrained embedding that is most similar to input visual embedding among pretrained embedding stored in the causal triple embedding & concept repository by using at least one of cosine similarity or Euclidean similarity, and the causal concept inference unit 209, which matches a concept in the extracted index based on the extracted index and the hash map stored in the causal triple embedding & concept repository 208, and transforms the matched concept into a sentence to output an associated causal expression.

For example, the cause miner 120 may perform cause mining by using abductive reasoning.

According to an example, at a learning (offline) stage, the modality-agnostic causality decoder 206 is trained so as to project visual embedding x to a predefined causal concept c.

According to an example, the modality-agnostic causality decoder 206 may include a sequential stack of m number of decoder layers, the addition layer 306 following a last decoder layer, and a softmax classifier 402.

For example, at least one decoder 401 each may include a sequential stack of a self-attention layer 403, the addition layer 306 for performing element-wise addition, a normalization layer 404, and at least one fully connected layer 405. Operation of the self-attention layer 403 that may be configured with a learnable query matrix $W_q$, key matrix $W_k$, and value matrix $W_v$ that matches the visual embedding x in terms of dimension may be expressed as the following equation.

$$Q = X \times W_q \qquad \text{[Equation 1]}$$

$$K = X \times W_k$$

$$V = X \times W_V$$

$$M = \frac{Q \times K^T}{\sqrt{d_K}}$$

$$S = \text{Softmax}\,(M) = \frac{e^M}{\sum_{j=1}^{d_M} e^M}$$

$$Z = S \times V$$

Where Q, K, V, M, S, and Z denote extracted intermediate embedding matrices, and $d_K$ and $d_M$ respectively denote dimensions of K and M matrices. For example, it may be understood that, through self-attention, an input X itself is manipulated by different learnable matrices so that a coefficient of a higher value is assigned as a weight to an important item of embedding to pay more attention thereto, and a less important item is multiplied by a coefficient of a lower value so as to be attenuated.

For example, the addition layer 306 involves in reuse of the initial input X in order to prevent encoded information from being unexpectedly omitted. Thereafter, stability of a characteristic learning process may be improved by expanding an item of input embedding to a value between 0 and 1 by applying the normalization layer 404. Thereafter, at least one fully connected layer 402 may be performed in order to complete a function learned in the decoder layer.

According to an embodiment, with regard to a task workflow outside the decoder layer, an output $Y_i$ (i=1, ... X) from each decoder layer is added in the addition layer 306, and this may maintain a reusable state of a function obtained at a different decoding stage, thereby allowing the following softmax classifier 402 to obtain a larger amount of information about differentiation between different causal concepts for X.

According to an example, the modality-agnostic causality decoder 206 may store, in the causal triple embedding & concept repository 208, mapping between input causal embedding and a causal concept in a form of a key-value pair.

According to an example, at a reasoning (online) stage, the cause miner 120 may extract a causal concept from visual embedding. For example, the nearest causal candidate retriever 207 may collect, from the causal triple embedding & concept repository 208, a best predetermined index of embedding that is most similar to input visual embedding through a comparison using cosine/Euclidean similarity measures 406. Thereafter, causal concept inference may be activated so that an associated predetermined cause may be output through a sequential task of an index-to-concept mapper 407 and concept-to-sentence transformation 408. In particular, the index-to-concept mapper 407 may calculate a best causal concept corresponding to the best predetermined index retrieved in a previous task by scanning a predefined hash map including a pair of an index (namely, key) and causal concept (namely, value). Thereafter, concept-to-sentence transformation is triggered so that a causal concept in a triple form of subject (cause)+verb+object (effect) may be transformed into a human friendly sentence indicating a predetermined cause.

FIG. 5 is a configuration diagram illustrating a logical reasoner according to an embodiment.

According to an embodiment, the logical reasoner 130 may include the multimodal recognizer 212, which generates multimodal embedding based on visual embedding, text embedding, and graph-based embedding, and generates a diagnosis label based on the multimodal embedding, and the pathological reasoner 213, which generates a logical concept based on the diagnosis label and pathological logic, and generates a medical report by transforming a pathological meta rule generated based on the logical concept and a predetermined cause into a natural language.

According to an example, the logical reasoner 130 may perform inductive reasoning. Referring to FIG. 5, the logical reasoner 130 may be configured with two components, i.e., the multimodal recognizer 212 functioning as another neural learning procedure and the pathological reasoner 213 performing according to a symbolic reasoning mechanism.

According to an example, the multimodal recognizer 212 may obtain a plurality of inputs including visual embedding, text embedding, and background knowledge graph. The multimodal recognizer 212 may include a graph neural network 501, and may implicitly transform the background knowledge graph 211 into a numerical expression, i.e., graph-based embedding for expressing a complicated relationship between all nodes (vertices) and edges of a graph. A multimodal attention layer 502 may generate multimodal embedding by obtaining visual embedding, text embedding, and pre-inferred graph-based embedding. An operation stage of the multimodal attention layer 502 is mostly similar to the self-attention layer of Equation 1, but is different in that Q, K, and V are calculated at a different input (text embedding and previously inferred graph-based embedding) that is visual embedding. For example, a classifier 503 may provide a diagnosis label with regard to a ground truth annotation of a training data set.

According to an example, the background knowledge graph 211 may be used to construct a pathology-specific logic pool 504 including pathology-related context at various nodes and edges of a knowledge graph. For example, at least one disease category or severity may be attached to input data together with related visual or textual detailed information. For example, a specific disease A may be associated with presence of anomaly in a specific region of a medical image.

According to an example, a first order logic programming layer 505 may obtain a diagnosis label based on a pathological logic received from the classifier 503 and the pathology-specific logic pool 504 as a variable and function for deriving a well-formed formula defined by predicate, equation, negation, binary conjunction, quantifier symbol, etc. For example, an output from the first order logic programming layer 505 may be a logical concept in a form of symbolic expression showing all possible associations between a diagnosed disease label and collective physical or psychological occurrence of an abnormal sign, symptom, medical condition, description or input data.

According to an example, a relationship hypothesis induction layer 506 may obtain an inferred predetermined cause 210 together with a logical concept to generate a pathological meta rule from a temporal and spatial perspective including all aspects describing a cause of severity beyond visual content.

According to an example, a textual inference layer 507 may generate a medical report by transforming the pathological meta rule into a natural language. This report may comprehensively explain human-interpretable inference and all pathological findings pertaining to visual content of an input medical image.

Figure 6:
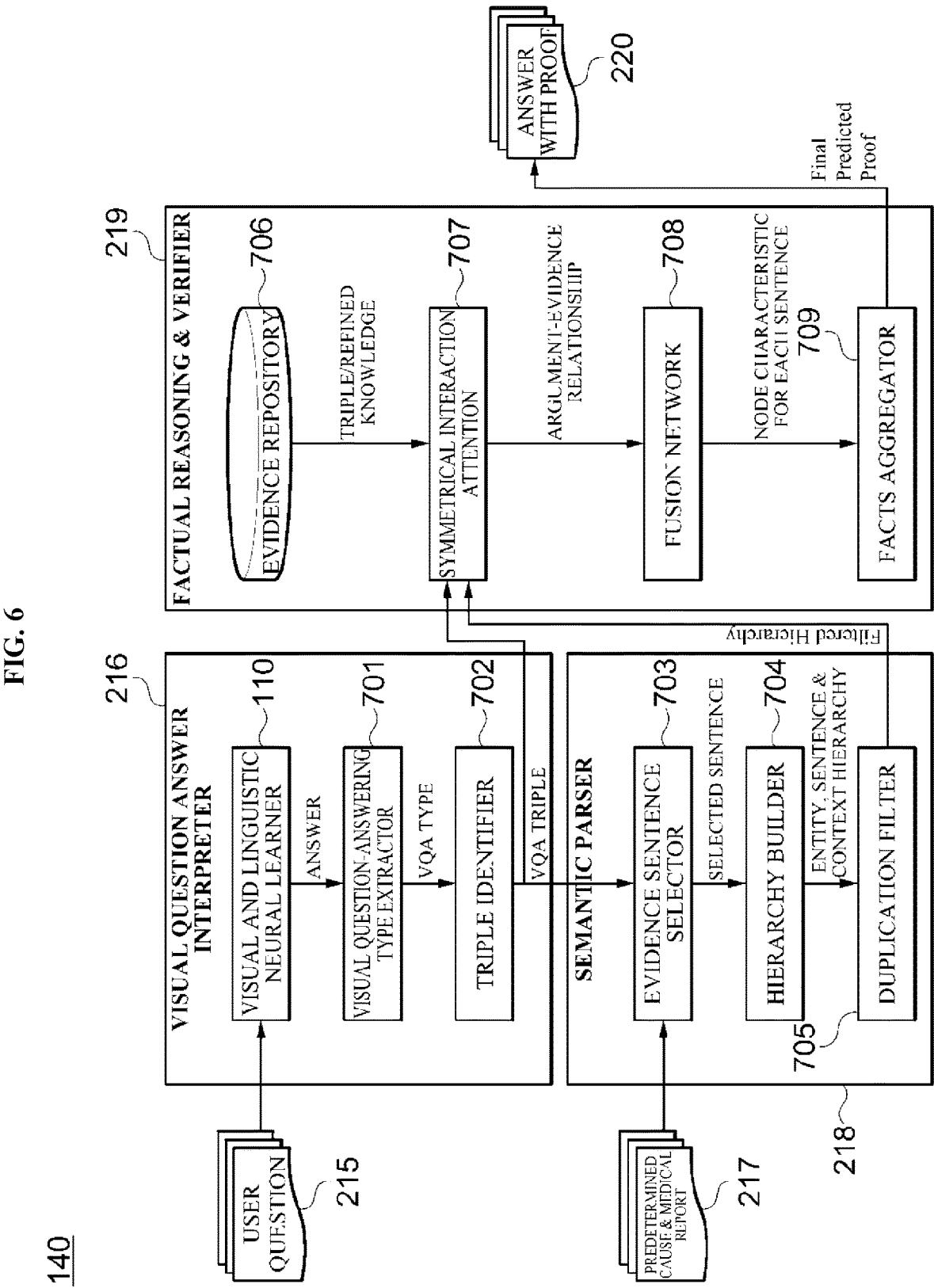
FIG. 6 is a configuration diagram illustrating a proof inference unit according to an embodiment.

FIG. 6 is a configuration diagram illustrating a proof inference unit according to an embodiment.

According to an embodiment, the proof inference unit 140 may include the visual question answer interpreter 216, which receives an input of a user's question about a medical image, extracts the type of a visual question and answer, and determines a visual question answer (VQA) triple according to a VQA type, the semantic parser 218, which receives an input of the VQA triple, a predetermined cause, and a medical report, extracts a sentence related to a visual question answer from the predetermined cause and the medical report, and constructs a hierarchy in a form of entity, sentence, and context for the extracted sentence, and the factual reasoning & verifier 219, which receives an input of the VQA triple and a duplication-filtered hierarchy in a form of entity, sentence, and context, and generates a proof for the user's question.

For example, the proof inference unit 140 may receive at least one pathological question related to visual content that is a medical image from a user who is a doctor, and may process a VQA scenario that may have high robustness and reliability in clinical practice. That is, the proof inference unit 140 may quickly generate an answer through proof support so as to accelerate an existing diagnosis procedure while securing accuracy and transparency.

According to an example, the visual question answer interpreter 216 may generate an answer corresponding to an input question about specific visual content of a medical image by adopting the visual and linguistic neural learner 110 pretrained with a VQA task. A visual question-answering type extractor 701 may extract the type of a visual question and answer. Thereafter, a triple identifier 702 may determine a triple according to a VQA type. The triple identifier 702 may be a generative pretrained transformer (GPT) or bidirectional encoder representations from transformers (BERT).

According to an example, the semantic parser 218 may use identified triple information, an inferred predetermined cause, and a medical report as a input for a next task.

For example, an evidence sentence selector 703 may be configured with a pretrained different language model such as a GPT or BERT. The evidence sentence selector 703 may identify a related sentence in the predetermined cause and the medical report.

For example, a hierarchy builder 704 may construct a hierarchy in a form of entity, sentence, and context using a designated language model. A duplication filter 705 filters the hierarchy at each level of the hierarchy using a predefined gating mechanism, and the filtered hierarchy may be delivered to the factual reasoning & verifier 219.

According to an example, in the factual reasoning & verifier 219, an evidence repository 706 may provide triple/refined knowledge for each predefined domain aside from the VQA triple extracted by the triple identifier 702 and the filtered hierarchy obtained as an input to a symmetrical interaction attention layer 707.

According to an example, a fusion network 708 constructed based on multilayer perceptron may receive an argument-evidence relationship identified in a form of a feature vector in order to process information propagation between evidences. Each node of the fusion network 708 may represent one evidence, and, in this manner, a node characteristic may be generated for each evidence sentence.

According to an example, a facts aggregator 709 may determine at least one specific proof present in an inferred result (i.e., predetermined cause and medical report) supporting an inferred answer by performing an evaluation procedure between evidence sentences after combining all node functions. In this manner, the facts aggregator 709 may provide an answer with a proof to a doctor in a reliable and convincible manner.

FIG. 7 is a flowchart illustrating a medical decision supporting method according to an embodiment.

According to an embodiment, a medical decision supporting apparatus may receive a medical image and extract visual embedding (710). Thereafter, the medical decision supporting apparatus may extract a predetermined index based on the visual embedding and pretrained embedding (720), and may output a predetermined cause for the medical image based on the extracted predetermined index and a hash map including at least one index-concept pair (730).

The medical decision supporting apparatus may generate a medical report based on the visual embedding, a background knowledge graph, and the predetermined cause (740), and may generate an answer with a proof for a user's question about the medical image based on the predetermined cause and the medical report (750).

According to an example, the medical decision supporting apparatus may extract visual embedding from a medical image, may extract text embedding from text data about the medical image, and may extract multimodal embedding based on the visual embedding and the text embedding.

According to an example, the medical decision supporting apparatus may include a visual encoder including at least one convolutional layer including a convolutional kernel, batch normalization layer, and nonlinear activation layer, and a global pooling layer, and a text encoder including a word embedding layer, a positional embedding layer, and an addition layer. Furthermore, the medical decision supporting apparatus may include at least one decoder, wherein each of the at least one decoder may include a cross-modal decoder, which outputs multimodal embedding based on at least one of visual embedding that is an output from the visual encoder, text embedding that is an output from the text encoder, or multimodal embedding that is an output form a previous-stage decoder.

For example, the medical decision supporting apparatus may receive an input of visual embedding, may output a causal concept, may store the visual embedding and causal concept, may extract an index of pretrained embedding that is most similar to input visual embedding among pretrained embedding stored in a causal triple embedding & concept repository by using at least one of cosine similarity or Euclidean similarity, may match a concept in the extracted index based on the extracted index and a hash map stored in the causal triple embedding & concept repository, and may transform the matched concept into a sentence to output an associated causal expression.

According to an example, the medical decision supporting apparatus may generate multimodal embedding based on visual embedding, text embedding, and graph-based embedding, may generate a diagnosis label based on the multimodal embedding, may generate a logical concept based on the diagnosis label and pathological logic, and may generate a medical report by transforming a pathological meta rule generated based on the logical concept and a predetermined cause into a natural language.

According to an example, the medical decision supporting apparatus may receive an input of a user's question about a medical image, may extract the type of a visual question and answer, may determine a visual question answer (VQA) triple according to a VQA type, may receive an input of the VQA triple, a predetermined cause, and a medical report, may extract a sentence related to a visual question answer from the predetermined cause and the medical report, may construct a hierarchy in a form of entity, sentence, and context for the extracted sentence, may receive an input of the VQA triple and a duplication-filtered hierarchy in a form of entity, sentence, and context, and may generate a proof for the user's question.

Descriptions of the embodiment of FIG. 7 which overlap the descriptions provided with reference to FIGS. 1 to 6 are omitted.

Figure 8:
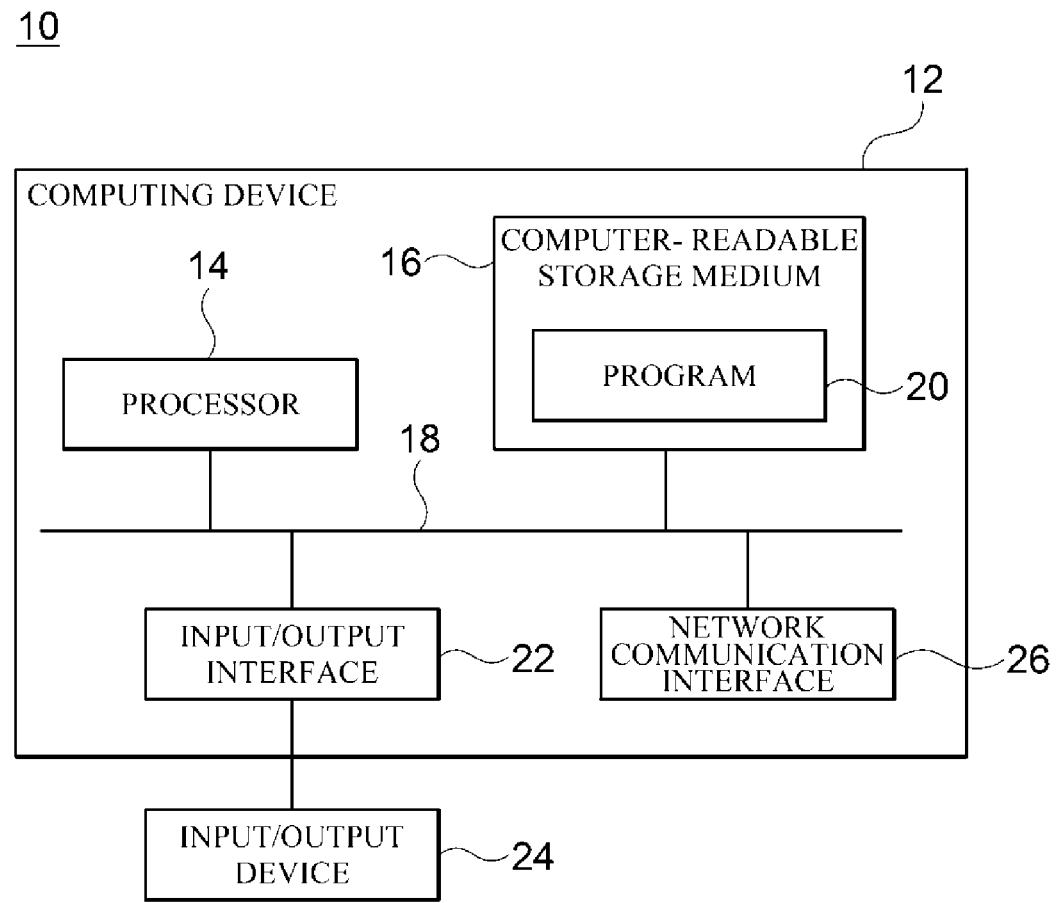
FIG. 8 is a block diagram illustrating a computing environment that includes a computing device suitable for use in example embodiments.

FIG. 8 is a block diagram illustrating a computing environment 10 that includes a computing device suitable for use in example embodiments. In the illustrated embodiment, each component may have different functions and capabilities in addition to those described below, and additional components may be included in addition to those described below.

The illustrated computing environment 10 includes a computing device 12. In an embodiment, the computing device 12 may be the medical decision supporting apparatus 100.

The computing device 12 includes at least one processor 14, a computer-readable storage medium 16, and a communication bus 18. The processor 14 may cause the computing device 12 to operate according to the above-described example embodiments. For example, the processor 14 may execute one or more programs stored in the computer-readable storage medium 16. The one or more programs may include one or more computer-executable instructions, which may be configured to cause, when executed by the processor 14, the computing device 12 to perform operations according to the example embodiments.

The computer-readable storage medium 16 is configured to store computer-executable instructions or program codes, program data, and/or other suitable forms of information. A program 20 stored in the computer-readable storage medium 16 includes a set of instructions executable by the processor 14. In an embodiment, the computer-readable storage medium 16 may be a memory (a volatile memory such as a random access memory, a non-volatile memory, or any suitable combination thereof), one or more magnetic disk storage devices, optical disk storage devices, flash memory devices, other types of storage media that are accessible by the computing device 12 and store desired information, or any suitable combination thereof.

The communication bus 18 interconnects various other components of the computing device 12, including the processor 14 and the computer-readable storage medium 16.

The computing device 12 may also include one or more input/output interfaces 22 that provide an interface for one or more input/output devices 24, and one or more network communication interfaces 26. The input/output interface 22 and the network communication interface 26 are connected to the communication bus 18. The input/output device 24 may be connected to other components of the computing device 12 via the input/output interface 22. The example input/output device 24 may include a pointing device (a mouse, a trackpad, or the like), a keyboard, a touch input device (a touch pad, a touch screen, or the like), a voice or sound input device, input devices such as various types of sensor devices and/or imaging devices, and/or output devices such as a display device, a printer, a speaker, and/or a network card. The example input/output device 24 may be included inside the computing device 12 as a component constituting the computing device 12, or may be connected to the computing device 12 as a separate device distinct from the computing device 12.

An answer including a proof for a medical image may be provided so that a user may use an analysis result with reliability.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A medical decision supporting apparatus comprising:
    a visual and linguistic neural learner configured to receive
        a medical image and extract visual embedding;

a cause miner configured to extract a predetermined index based on the visual embedding and pretrained embedding, and output a predetermined cause for the medical image based on a hash map including at least one index-concept pair and the extracted predetermined index;

a logical reasoner configured to generate a medical report based on the visual embedding, a background knowledge graph, and the predetermined cause; and a proof inference unit configured to generate an answer including a proof for a user's question about the medical image based on the predetermined cause and the medical report, wherein the visual and linguistic neural learner comprises:

a visual encoder configured to extract the visual embedding from the medical image;

a text encoder configured to extract text embedding from text data about the medical image; and a cross-modal decoder configured to extract multimodal embedding based on the visual embedding and the text embedding, wherein the cause miner comprises:

a modality-agnostic causality decoder configured to receive an input of the visual embedding and output a causal concept;

a causal triple embedding & concept repository configured to store the visual embedding and the causal concept;

a nearest causal candidate retriever configured to extract an index of pretrained embedding that is most similar to input visual embedding among pretrained embedding stored in the causal triple embedding & concept repository by using at least one of cosine similarity or Euclidean similarity; and a causal concept inference unit configured to match a concept in the extracted index based on the extracted index and the hash map stored in the causal triple embedding & concept repository, and transform the matched concept into a sentence to output an associated causal expression.

2. The medical decision supporting apparatus of claim 1, wherein the visual encoder comprises at least one convolutional layer including a convolutional kernel, batch normalization layer, and nonlinear activation layer, and a global pooling layer.

3. The medical decision supporting apparatus of claim 1, wherein the text encoder comprises a word embedding layer, a positional embedding layer, and an addition layer.

4. The medical decision supporting apparatus of claim 1, wherein the cross-modal decoder comprises at least one decoder, wherein each of the at least one decoder outputs the multimodal embedding based on at least one of the visual embedding that is an output from the visual encoder, the text embedding that is an output from the text encoder, or multimodal embedding that is an output form a previous-stage decoder.

5. The medical decision supporting apparatus of claim 1, wherein the logical reasoner comprises:

a multimodal recognizer configured to generate multimodal embedding based on the visual embedding, text embedding, and graph-based embedding, and generate a diagnosis label based on the multimodal embedding; and a pathological reasoner configured to generate a logical concept based on the diagnosis label and pathological logic, and generate the medical report by transforming a pathological meta rule generated based on the logical concept and the predetermined cause into a natural language.

6. A medical decision supporting apparatus comprising:

a visual and linguistic neural learner configured to receive a medical image and extract visual embedding;

a cause miner configured to extract a predetermined index based on the visual embedding and pretrained embedding, and output a predetermined cause for the medical image based on a hash map including at least one index-concept pair and the extracted predetermined index;

a logical reasoner configured to generate a medical report based on the visual embedding, a background knowledge graph, and the predetermined cause; and a proof inference unit configured to generate an answer including a proof for a user's question about the medical image based on the predetermined cause and the medical report, wherein the proof inference unit comprises:

a visual question answer interpreter configured to receive an input of the user's question about the medical image, extract a type of a visual question and answer, and determine a visual question answer (VQA) triple according to a VQA type;

a semantic parser configured to receive an input of the VQA triple, the predetermined cause, and the medical report, extract a sentence related to the visual question answer from the predetermined cause and the medical report, and construct a hierarchy in a form of entity, sentence, and context for the extracted sentence; and a factual reasoning & verifier configured to receive an input of the VQA triple and a duplication-filtered hierarchy in a form of entity, sentence, and context, and generate a proof for the user's question.

7. A medical decision supporting method performed by a computing device having at least one processor and a memory that stores at least one program executed by the at least one processor, the method comprising:

a visual and linguistic neural learning step of receiving a medical image and extracting visual embedding;

a cause mining step of extracting a predetermined index based on the visual embedding and pretrained embedding, and outputting a predetermined cause for the medical image based on a hash map including at least one index-concept pair and the extracted predetermined index;

a logical reasoning step of generating a medical report based on the visual embedding, a background knowledge graph, and the predetermined cause; and a proof inference step of generating an answer including a proof for a user's question about the medical image based on the predetermined cause and the medical report, wherein the cause mining step comprises:

receiving an input of the visual embedding and outputting a causal concept;

storing the visual embedding and the causal concept;

extracting an index of pretrained embedding that is most similar to input visual embedding among pretrained embedding stored in a causal triple embedding & concept repository by using at least one of cosine similarity or Euclidean similarity;

matching a concept in the extracted index based on the extracted index and a hash map stored in the causal triple embedding & concept repository; and transforming the matched concept into a sentence to output an associated causal expression.

8. The medical decision supporting method of claim 7, wherein the visual and linguistic neural learning step comprises:

extracting the visual embedding from the medical image;

extracting text embedding from text data about the medical image; and extracting multimodal embedding based on the visual embedding and the text embedding.

9. The medical decision supporting method of claim 8, wherein in the visual and linguistic neural learning step, a visual encoder is used, which comprises at least one convolutional layer including a convolutional kernel, batch normalization layer, and nonlinear activation layer, and a global pooling layer.

10. The medical decision supporting method of claim 8, wherein in the visual and linguistic neural learning step, a text encoder is used, which comprises a word embedding layer, a positional embedding layer, and an addition layer.

11. The medical decision supporting method of claim 8, wherein in the visual and linguistic neural learning step, a cross-modal decoder is used, which comprises at least one decoder, wherein each of the at least one decoder outputs the multimodal embedding based on at least one of the visual embedding that is an output from a visual encoder, the text embedding that is an output from a text encoder, or multimodal embedding that is an output form a previous-stage decoder.

12. The medical decision supporting method of claim 7, wherein the logical reasoning step comprises:

generating multimodal embedding based on the visual embedding, text embedding, and graph-based embedding, and generating a diagnosis label based on the multimodal embedding; and generating a logical concept based on the diagnosis label and pathological logic, and generating the medical report by transforming a pathological meta rule generated based on the logical concept and the predetermined cause into a natural language.

13. A medical decision supporting method performed by a computing device having at least one processor and a memory that stores at least one program executed by the at least one processor, the method comprising:

a visual and linguistic neural learning step of receiving a medical image and extracting visual embedding;

a cause mining step of extracting a predetermined index based on the visual embedding and pretrained embedding, and outputting a predetermined cause for the medical image based on a hash map including at least one index-concept pair and the extracted predetermined index;

a logical reasoning step of generating a medical report based on the visual embedding, a background knowledge graph, and the predetermined cause; and a proof inference step of generating an answer including a proof for a user's question about the medical image based on the predetermined cause and the medical report, wherein the proof inference step comprises:

receiving an input of the user's question about the medical image, extracting a type of a visual question and answer, and determining a visual question answer (VQA) triple according to a VQA type;

receiving an input of the VQA triple, the predetermined cause, and the medical report, extracting a sentence related to the visual question answer from the predetermined cause and the medical report, and constructing a hierarchy in a form of entity, sentence, and context for the extracted sentence; and receiving an input of the VQA triple and a duplication-filtered hierarchy in a form of entity, sentence, and context, and generating a proof for the user's question.

14. A computer program stored in a non-transitory computer readable storage medium, the computer program comprising one or more instructions that, when executed by a computing device having at least one processor, cause the computing device to execute:

a visual and linguistic neural learning step of receiving a medical image and extracting visual embedding;

a cause mining step of extracting a predetermined index based on the visual embedding and pretrained embedding, and outputting a predetermined cause for the medical image based on a hash map including at least one index-concept pair and the extracted predetermined index;

a logical reasoning step of generating a medical report based on the visual embedding, a background knowledge graph, and the predetermined cause; and a proof inference step of generating an answer including a proof for a user's question about the medical image based on the predetermined cause and the medical report, wherein the cause mining step comprises:

receiving an input of the visual embedding and outputting a causal concept;

storing the visual embedding and the causal concept;

extracting an index of pretrained embedding that is most similar to input visual embedding among pretrained embedding stored in a causal triple embedding & concept repository by using at least one of cosine similarity or Euclidean similarity;

matching a concept in the extracted index based on the extracted index and a hash map stored in the causal triple embedding & concept repository; and transforming the matched concept into a sentence to output an associated causal expression.

* * * * *